United States Patent [19]

Strukel

[11] Patent Number: 5,358,477
[45] Date of Patent: Oct. 25, 1994

[54] DIFFERENTIAL PRESSURE ADMINISTRATION SET

[75] Inventor: Igor Strukel, New York, N.Y.
[73] Assignee: Surgical Design Corporation, Long Island City, N.Y.
[21] Appl. No.: 82,604
[22] Filed: Jun. 25, 1993
[51] Int. Cl.$^5$ .............................................. A61M 5/14
[52] U.S. Cl. ......................................... 604/80; 604/89
[58] Field of Search ................... 222/94, 431; 604/80, 604/81, 82, 85, 89, 31, 296, 298, 118

[56] References Cited

U.S. PATENT DOCUMENTS 4,019,514  4/1977  Banko .
4,043,332  8/1977  Metcalf ............................... 604/118
4,417,577 11/1983  Genese et al. ........................ 604/31

*Primary Examiner*—C. Fred Rosenbaum
*Assistant Examiner*—N. Kent Gring
*Attorney, Agent, or Firm*—Darby & Darby

[57] ABSTRACT

A differential pressure administration set having a tubular chamber, which has an inlet at its upper end connected to a liquid supply container. Below the inlet is a first chamber which receives liquid from the container. Near or at the bottom of the first chamber is an outlet supply line to provide the higher pressure liquid to the operating site. The first chamber also has a second outlet which feeds liquid to a second chamber below the first chamber. There is a second outlet supply line at the lower end of the second chamber, which provides the lower pressure liquid to the operating site. The differential pressure is produced by and corresponds to the difference in height between the levels of the fluids in the first and second chambers.

8 Claims, 2 Drawing Sheets

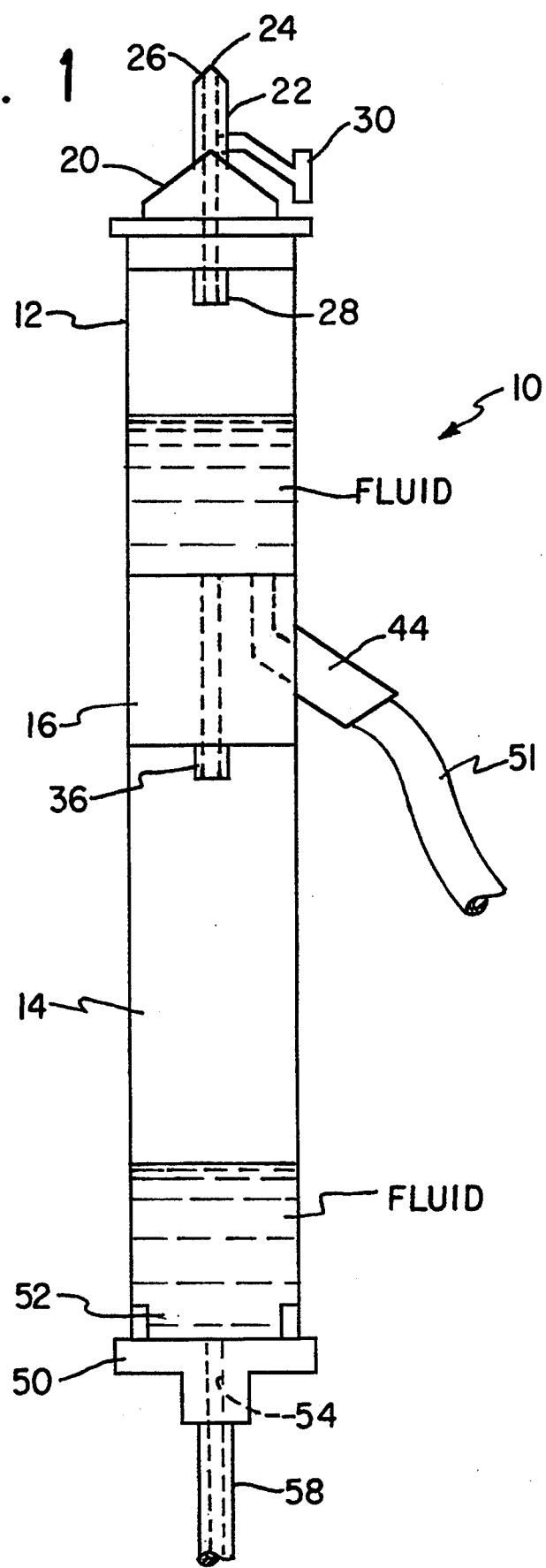

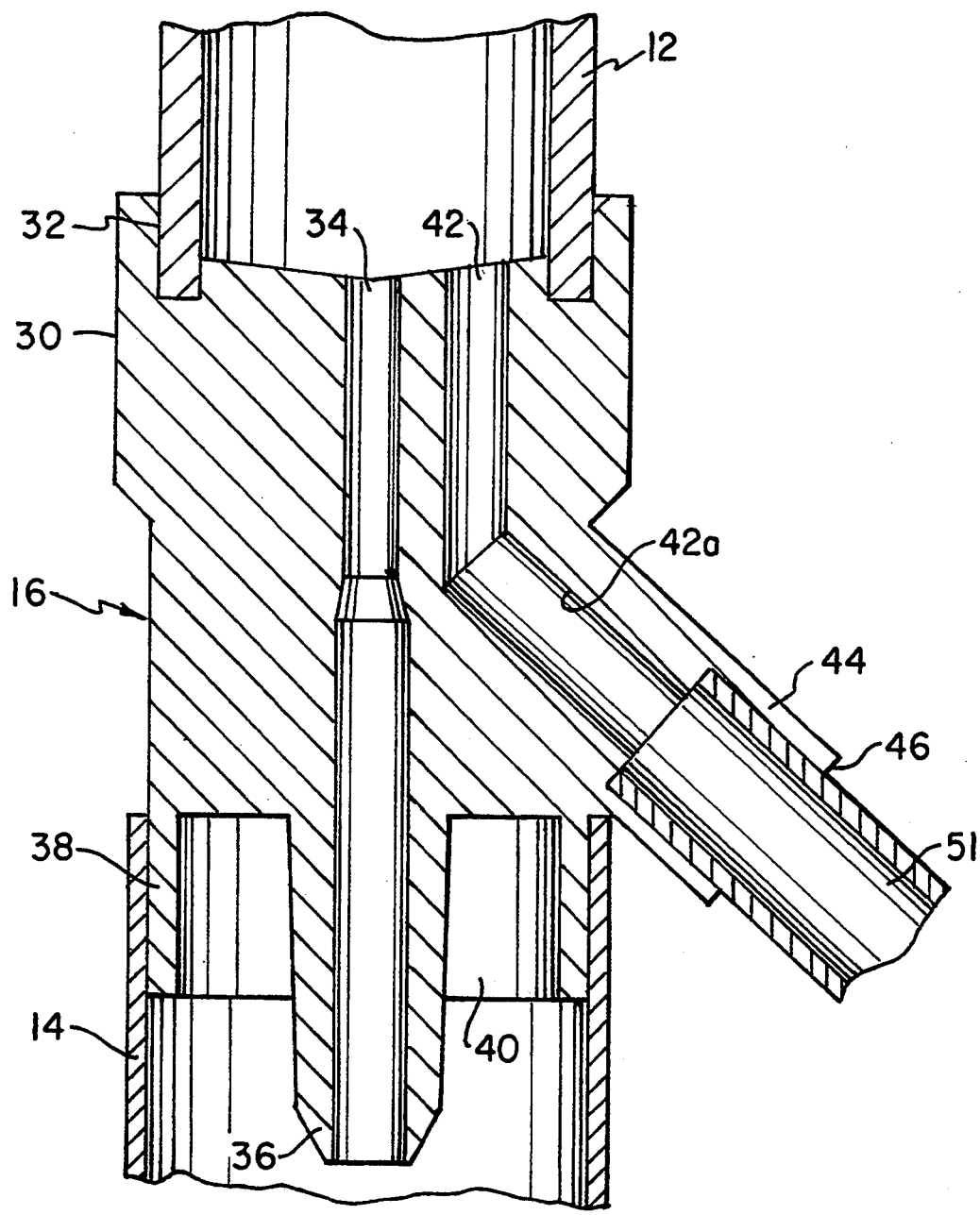

DIFFERENTIAL PRESSURE ADMINISTRATION SET

BACKGROUND OF THE INVENTION

In certain medical applications, it is desired to supply liquids at two different pressures to an operating instrument. Typical of this is, for example, U.S. Pat. No. 4,019,514, granted to Anton Banko, which is assigned to the assignee of this application, which discloses an instrument for opthamologic surgery. In that patent, two liquid lines are needed, one to supply the instrument with liquid at a first pressure, such as for infusion and a reverse flow liquid which is at pressure higher than the first pressure. Combined with the geometry of the surgical instrument, the higher pressure fluid forces unwanted material to be removed from the surgical site.

Heretofore, this has been accomplished by using two separate containers for the liquid. The container for supplying the higher pressure reverse flow liquid is placed at a higher position than the lower pressure infusion liquid. While such arrangement is operative, it is somewhat cumbersome since two separate liquid containers and two separate liquid lines from the separate liquid containers to the operating instrument must be provided. In addition, it is more difficult to determine the amount of fluid used, since the flow out of two containers must be added. Confirming proper flow from the two containers is also more cumbersome with the previous systems, since two drip chambers, remote from each other, must be observed.

BRIEF DESCRIPTION OF THE PRESENT INVENTION

The present invention relates to an administration set which can be used to provide liquids to an operating site at two different pressures. The administration set utilizes only one liquid supply container and automatically develops the two different necessary pressures.

In accordance with the invention a tubular chamber has an inlet at its upper end connected to a liquid supply container. Below the inlet is a first chamber which receives liquid from the container. Near or at the bottom of the first chamber is an outlet supply line to provide the higher pressure liquid to the operating site. The first chamber also has a second outlet which feeds liquid to a second chamber below the first chamber. There is a second outlet supply line at the lower end of the second chamber, which provides the lower pressure liquid to the operating site. The differential pressure is produced by and corresponds to the difference in height between the levels of the fluids in the first and second chambers.

OBJECT OF THE INVENTION

It is an object of this invention to provide a differential pressure administration set.

A further object is to provide a differential pressure administration set for delivering liquid at two different pressures from a single container.

Another object is to provide a differential pressure set for receiving liquid from a single liquid supply container and for delivering it at two separate outlets at two different pressures, one higher than the other.

An additional object of the present invention is to provide an administration set for use with medical instruments for developing two separate liquid pressures.

Still a further object is to provide an administration set operating from a single liquid source having two chambers, one to deliver liquid to an outlet line at a higher pressure and also to a second chamber from which the liquid is supplied to a second output line at a lower pressure.

BRIEF DESCRIPTION OF THE DRAWINGS

Other objects and advantages of the present invention will become more apparent upon reference to the following specification and annexed drawings in which:

FIG. 1 is an elevational view of the administration set of the present invention; and FIG. 2 is a cross-sectional view along lines 2—2 FIG. 1 showing the connection for the two chambers.

DETAILED DESCRIPTION OF THE INVENTION

The administration set of the present invention has a housing 10 formed by an upper and a lower tubular members 12 and 14. The two tubular members 12 and 14 are preferably held together by a connector 16 described in detail below.

An inlet connector 20 partially closes off the upper end of the first tubular member 12. Connector 20 has a through passage formed by hollow tube 22 with a tapered upper end 24 which can be pierced into the container holding the liquid supply (not shown) or over which a supply tube from the container can be placed. The connector tube 22 has an opening 26 at its upper end into which the liquid from the liquid supply container flows. At the lower end of connector 20 is an outlet tube 28.

An air vent 30 communicates with the passage through the connector 20 and preferably includes a filter not shown. Air is admitted into the upper tubular member through the slits of the air vent 30.

At the lower end of the first tubular member is a connector 16 (see FIG. 2). The connector 16 preferably has a peripheral shoulder 30 at its upper end defining a circular groove 32 into which fits the lower end of the first tubular member 12. The first tubular member can be held in the groove 32 by any suitable adhesive.

A passage 34 extends through the body of the connector 16 terminating at an extending outlet port 36 at the lower end of the connector 16. A downwardly facing peripheral shoulder 38 is also located at the lower end of connector 16 and defines a second internal groove 40. The upper end of the second tubular member 14 fits over the shoulder 38 and can be held there by any suitable adhesive.

An outlet 42 near the top end of connector 16 extends generally vertically from the connector 16 and then branches off at an angle section 42a. The angle section 42a terminates with a recess having an outer wall 44 into which fits a first liquid outlet supply line 51. Due to the elevation of the liquid in the upper member 12, the outlet supply line 51 provides the liquid from the first chamber 12 at a first pressure to an instrument (not shown) at an operating site. The instrument can be, for example, a phaecoemulsifier. With such an instrument, the first relatively high pressure liquid is used as the reverse flow to clear a passage or to equalize pressure in the infusion liquid supply line.

The fluid from the first chamber (which is defined by the first tubular member 12) also exits through the outlet port 36 of the connector 16 into the second tubular member 14. At the lower end of the second chamber 14 is an outlet connector 50 having a peripheral wall 52 over which the lower end of the second tubular member 14 fits and held by any suitable adhesive. The lower outlet connector 50 has an outlet fitting 54 onto which the second liquid line 58 is attached. Fluid from the second outlet line 58 is also fed to the instrument but at a second pressure lower than the fluid from the first outlet line 50. This would be, for example, the infusion liquid for the instrument. The lower pressure is due to the difference in heights of the two outlets and the water columns formed within the chambers. The pressure difference can also be altered by having unequal amounts of liquid in the two chambers, so it is preferred that the water amounts be kept relatively close to each other.

During operation of the administration set, a connection is made to the inlet connector 20 either by inserting it directly into the liquid supply container, or by connecting an inlet supply line onto the tube 20. The fluid from the supply container flows through the outlet 28 of the connector 20 into the first tubular member 12 and into the connector 16 at the bottom end of the member 12. The air entering the first member 12 through the vent fitting 30 replaces the liquid. The liquid at the connector 16 flows out of member 12 by two outlets, first through its outlet port 36 into the second tubular member 14, and also through the outlet passage 42a and through the outlet port 44 into the first outlet line 50.

The liquid which flows into the second tubular member 14 passes through the outlet 54 into the second outlet line 58. The fluid in the second outlet line 58 is at a lower pressure than the liquid in the first line 50.

Thus, the novel differential pressure administration set of the present invention provides fluid at two different pressures from a single unit that operates from a single fluid supply source.

The administration set of the present invention is relatively inexpensive and can be used on a disposable basis. That is, it would be provided pre-sterilized and it can be disposed of after the patient has been treated.

While the embodiments shown and described are fully capable of achieving the above-mentioned objects and advantages of the present invention, it is to be understood that these embodiments are shown for the purpose of illustration and not for the purpose of limitation, the invention being only limited by the claims, as follows:

What is claimed is:

1. A differential pressure administration set comprising:
   an elongated tubular member;
   separation means being disposed intermediate a vertical length of said tubular member and defining upper and lower chambers;
   inlet means at the upper end of said tubular member for admitting liquid into the upper chamber,
   said separation means having a first outlet for supplying the liquid from the upper chamber into the second chamber and a second outlet for supplying the liquid from the upper chamber to an external device, and
   outlet means at the lower end of said tubular member for supplying the liquid from the lower chamber to the external device simultaneously with the liquid being supplied from said second outlet.

2. An administration set as in claim 1 wherein said elongated tubular member comprises first and second sections, said first and second sections being attached to said separation means.

3. A differential pressure administration set comprising:
   an elongated tubular member;
   separation means being disposed intermediate a vertical length of said tubular member and defining upper and lower chambers:
   inlet means at the upper end of said tubular member for admitting liquid into the upper chamber,
   said separation means having a first outlet for supplying the liquid from the upper chamber into the second chamber and a second outlet for supplying the liquid from the upper chamber to an external device;
   outlet means at the lower end of said tubular member for supplying the liquid from the lower chamber to the external device; and
   said separation means comprises a connector having a central through passage for said first outlet and an outwardly extending arm with a passage for said second outlet.

4. A differential pressure administration set comprising:
   an elongated tubular member;
   separation means being disposed intermediate the vertical length of said tubular member and defining upper and lower chambers;
   inlet means at the upper end of said tubular member for admitting liquid into the upper chamber,
   said separation means having a first outlet for supplying the liquid from the upper chamber into the second chamber and a second outlet for supplying the liquid from the upper chamber to an external device;
   outlet means at the lower end of said tubular member for supplying the liquid from the lower chamber to the external device;
   said elongated tubular member comprises first and second sections, said first and second sections being attached to said separation means; and
   said separation means comprises a connector having a central through passage for said first outlet and an outwardly extending arm with a passage for said second outlet.

5. A differential pressure administration set comprising:
   an elongated tubular member;
   separation means being disposed intermediate the vertical length of said tubular member and defining upper and lower chambers;
   inlet means at the upper end of said tubular member for admitting liquid into the upper chamber,
   said separation means having a first outlet for supplying the liquid from the upper chamber into the second chamber and a second outlet for supplying the liquid from the upper chamber to an external device, and
   outlet means at the lower end of said tubular member for supplying the liquid from the lower chamber to the external device; and
   said inlet means at the upper end of said tubular member further comprises air vent means for admitting air into said upper chamber.

6. An administration set as in claim 5 wherein said air vent means includes a filter.

7. An administration set as in claim 3 wherein said inlet means at the upper end of said tubular member further comprises air vent means for admitting air into said upper chamber.

8. An administration set as in claim 7 wherein said air vent means includes a filter.

* * * * *